(12) United States Patent
Ashe et al.

(10) Patent No.: US 12,274,515 B2
(45) Date of Patent: *Apr. 15, 2025

(54) ELECTROMAGNETIC POSITION MEASUREMENT SYSTEM WITH SENSOR PARASITIC LOOP COMPENSATION

(71) Applicant: Northern Digital Inc., Waterloo (CA)

(72) Inventors: Westley S. Ashe, Hinesburg, VT (US); Georg Brunner, Constance (DE)

(73) Assignee: Northern Digital Inc., Waterloo (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/526,566

(22) Filed: Dec. 1, 2023

(65) Prior Publication Data
US 2024/0108418 A1    Apr. 4, 2024

Related U.S. Application Data

(63) Continuation of application No. 17/345,901, filed on Jun. 11, 2021, now Pat. No. 11,883,115.
(Continued)

(51) Int. Cl.
*A61B 5/00* (2006.01)
*A61B 5/06* (2006.01)
(Continued)

(52) U.S. Cl.
CPC .............. *A61B 34/20* (2016.02); *A61B 5/062* (2013.01); *G01V 3/10* (2013.01); *A61B 2034/2072* (2016.02)

(58) Field of Classification Search
CPC .. A61B 2034/2051; A61B 34/20; A61B 5/062
See application file for complete search history.

(56) References Cited

U.S. PATENT DOCUMENTS 5,982,645 A    11/1999    Levran et al.
6,177,792 B1    1/2001    Govari et al.
(Continued)

FOREIGN PATENT DOCUMENTS

CN    1901835    1/2007
CN    101410724    4/2009
(Continued)

OTHER PUBLICATIONS

[No Author Listed] [online], "3D Guidance Electromagnetic Needle Tip Tracking demo," NDI (Northern Digital Inc.), Dec. 17, 2019, retrieved on Feb. 2, 2022, URL<https://www.youtube.com/watch?app=desktop&v=PQM4_-cz8y8&feature=youtu.be>, 128 pages [Video Submission].

*Primary Examiner* — Rajeev P Siripurapu
(74) *Attorney, Agent, or Firm* — Fish & Richardson P.C.

(57) ABSTRACT

A magnetic tracking device includes a sensor configured to generate a sensor electromotive force (EMF). The device includes a mechanism configured to select between a first operating mode in which the sensor generates the sensor EMF when receiving the magnetic field and a second operating mode in which the sensor generates a reduced amount of the sensor EMF when receiving the magnetic field. An interconnecting circuit generates a parasitic EMF in each of the first operating mode and the second operating mode. The interconnecting circuit connects to a processing device which receives a first measurement for the first operating mode, the first measurement representing the sensor EMF and the parasitic EMF, receives a second measurement for the second operating mode, the second measurement representing the parasitic EMF, compares the first measurement and the second measurement, and determines an approximate value of the sensor EMF.

19 Claims, 7 Drawing Sheets

Related U.S. Application Data

(60) Provisional application No. 63/037,868, filed on Jun. 11, 2020.

(51) Int. Cl.
*A61B 34/20* (2016.01)
*G01V 3/10* (2006.01)

(56) References Cited

U.S. PATENT DOCUMENTS

| | | |
|---|---|---|
| 6,414,475 B1 | 7/2002 | Dames et al. |
| 6,498,477 B1 | 12/2002 | Govari et al. |
| 7,030,782 B2 | 4/2006 | Ely et al. |
| 7,088,984 B2 | 8/2006 | Oiwa |
| 7,612,427 B2 | 11/2009 | Erickson et al. |
| 8,629,572 B1 | 1/2014 | Phillips |
| 8,751,013 B2 | 6/2014 | Johnson et al. |
| 9,603,548 B2 | 3/2017 | Ashe |
| 11,883,115 B2 | 1/2024 | Ashe et al. |
| 2003/0117269 A1* | 6/2003 | Dimmer ............... A61B 34/20 340/572.1 |
| 2007/0244388 A1 | 10/2007 | Sato et al. |
| 2010/0113917 A1 | 5/2010 | Anderson |
| 2013/0249794 A1 | 9/2013 | Hutcheson et al. |
| 2014/0084905 A1 | 3/2014 | Shestakov |
| 2014/0369380 A1 | 12/2014 | Ausserlechner |
| 2015/0248944 A1 | 9/2015 | Cheng et al. |
| 2015/0346290 A1 | 12/2015 | Holm et al. |
| 2018/0081008 A1 | 3/2018 | Yang et al. |
| 2019/0226826 A1 | 7/2019 | Schneider et al. |
| 2019/0377412 A1 | 12/2019 | Parastegari et al. |
| 2020/0103992 A1 | 4/2020 | Sauer et al. |
| 2021/0386486 A1 | 12/2021 | Ashe et al. |

FOREIGN PATENT DOCUMENTS

| | | |
|---|---|---|
| CN | 203825190 | 9/2014 |
| CN | 104956190 | 9/2015 |
| CN | 105629315 | 6/2016 |
| EP | 0923802 | 12/2004 |
| JP | 5064826 | 10/2012 |
| JP | 2014106009 | 6/2014 |
| JP | 2017507742 | 3/2017 |

* cited by examiner

ELECTROMAGNETIC POSITION MEASUREMENT SYSTEM WITH SENSOR PARASITIC LOOP COMPENSATION

CROSS-REFERENCE TO RELATED APPLICATIONS

This application is a continuation application of and claims the benefit of priority to U.S. application Ser. No. 17/345,901, filed on Jun. 11, 2021, which claims priority to U.S. Patent Application Ser. No. 63/037,868, filed on Jun. 11, 2020, and the contents of each application is hereby incorporated by reference.

TECHNICAL FIELD

This disclosure relates to tracking one or more objects in a magnetic field, specifically a system for tracking a surgical instrument using electromagnetic (EM) signals.

BACKGROUND

Electromagnetic Tracking (EMT) systems are used to aid location of instruments and anatomy in medical procedures. Such systems can determine a position of a receiver based on measured field lines of a transmitted magnetic field.

SUMMARY

An Electromagnetic Tracking (EMT) system (also referred to as a magnetic tracking system) can be used to track a device for a number of applications, such as for medical applications during endoscope surgery or other types of surgery. The EMT system (also called a magnetic tracking system) includes at least one transmitter and at least one receiver. The transmitter emits, for example, a magnetic signal, and the receiver receives the magnetic signal and measures the magnetic signal. The measured magnetic signal provides information that the magnetic tracking system uses to determine relative locations of the transmitter with respect to the receiver (or vice versa). If the transmitter or receiver is affixed to another device (e.g., a tracked device), the magnetic tracking system can determine the relative location of the tracked device in the environment of the magnetic tracking system. In some implementations, the magnetic tracking system can detect distortions in the magnetic signal due to metallic objects in the environment. Numerous additional applications for tracking an object are known.

The techniques described herein include one or more of the following advantages. The magnetic tracking system is configured to more accurately determine what the position of the tracked device is by compensating for distortions in the magnetic signal. Placing visual markers around the environment of the magnetic tracking system for establishing a visual reference frame is a relatively low cost solution to compensate for magnetic distortions.

The magnetic tracking device can include on or more of the following embodiments. In a general aspect, a magnetic tracking device includes a sensor configured to generate a sensor electromotive force (EMF) that measures a magnetic field that is generated by a magnetic field transmitter. The magnetic tracking device includes a mechanism configured to select between a first operating mode in which the sensor generates the sensor EMF when receiving the magnetic field and a second operating mode in which the sensor generates a reduced (possibly zero) sensor EMF when receiving the magnetic field. The magnetic tracking device includes an interconnecting circuit configured generate a parasitic EMF in each of the first operating mode and the second operating mode when receiving the magnetic field. Generally, the interconnecting circuit is configured to connect (either directly or indirectly) to a processing device. The processing device configured to: receive a first measurement for the first operating mode, the first measurement representing the sensor EMF and the parasitic EMF. The processing device is configured to receive a second measurement for the second operating mode, the second measurement representing the parasitic EMF and the reduced sensor EMF. The processing device is configured to compare the first measurement and the second measurement. The processing device is configured to, based on comparing the first measurement and the second measurement, determine an approximate value of the sensor EMF.

In some implementations, the mechanism comprises a diode in parallel with the sensor coil, the diode configured to be reverse biased in the first operating mode and configured to be forward biased in the second operating mode. In some implementations, the diode is a first diode, the magnetic tracking device comprising a second diode in series with the sensor coil, wherein the second diode is configured to be forward biased in the first operating mode and configured to be reverse biased in the second operating mode. In some implementations, the mechanism comprises a switching device in parallel with the sensor coil, the switching device configured to be in a high impedance state in the first operating mode and configured to be in a low impedance state in the second operating mode.

In some implementations, the switching device comprises one of a junction gate field-effect transistor (JFET), metal-oxide-semiconductor field-effect transistor (MOSFET), a bipolar transistor, or a relay.

In some implementations, comparing the first measurement and the second measurement comprises determining a change an impedance of the interconnecting circuit in the second operating mode relative to the impedance of the interconnecting circuit in the first operating mode, and based on the determining, adjusting the approximate value of the sensor EMF.

In some implementations, the processing device is further configured to determine an approximate position of the sensor coil relative to a magnetic transmitter based on the approximate value of the sensor EMF.

In some implementations, the parasitic EMF comprises induced EMF values from an interconnect loop of the interconnecting circuit, a connector loop of the interconnecting circuit, a trace loop of the interconnecting circuit, or any combination thereof.

In some implementations, the magnetic tracking device includes a connector configured to connect the sensor coil to the processing device, the connector being a portion of the interconnecting circuit. In some implementations, processing device is configured to cause the mechanism to cycle between the first operating mode and the second operating mode in synchronization with a cycle of the magnetic field that is generated by the magnetic field transmitter.

In a general aspect, a magnetic tracking system includes a magnetic tracking device. The magnetic tracking device includes a sensor configured to generate a sensor electromotive force (EMF) that measures a magnetic field that is generated by a magnetic field transmitter. The magnetic tracking device includes a mechanism configured to select between a first operating mode in which the sensor generates the sensor EMF when receiving the magnetic field and a second operating mode in which the sensor generates a reduced sensor EMF when receiving the magnetic field. The magnetic tracking device includes an interconnecting circuit configured generate a parasitic EMF in each of the first operating mode and the second operating mode when receiving the magnetic field. The magnetic tracking system includes a processing device connected to the magnetic tracking device by the interconnected circuit. The processing device is configured to receive a first measurement for the first operating mode, the first measurement representing the sensor EMF and the parasitic EMF. The processing device is configured to receive a second measurement for the second operating mode, the second measurement representing the parasitic EMF and the reduced (possibly zero) sensor EMF. The processing device is configured to compare the first measurement and the second measurement. The processing device is configured to, based on comparing the first measurement and the second measurement, determine an approximate value of the sensor EMF.

In some implementations, the mechanism comprises a diode in parallel with the sensor, the diode configured to be reverse biased in the first operating mode and configured to be forward biased in the second operating mode. In some implementations, the mechanism comprises a switching device in parallel with the sensor coil, the switching device configured to be in a high impedance state in the first operating mode and configured to be in a low impedance state in the second operating mode. In some implementations, the switching device comprises one of a junction gate field-effect transistor (JFET), metal-oxide-semiconductor field-effect transistor (MOSFET), a bipolar transistor, or a relay.

In some implementations, the diode is a first diode, the magnetic tracking device comprising a second diode in series with the sensor, wherein the second diode is configured to be forward biased in the first operating mode and configured to be reverse biased in the second operating mode.

In some implementations, the magnetic tracking device is disposed inside of a catheter device. In some implementations, the magnetic tracking system includes a guidewire that includes interconnects of the interconnecting circuit and a core, wherein a radius the guidewire is a radius of the core and one diameter length of an interconnect of the interconnects.

In some implementations, the processing device is configured to cause the mechanism to cycle between the first operating mode and the second operating mode in synchronization with a cycle of the magnetic field that is generated by the magnetic field transmitter.

In a general aspect, the magnetic tracking device includes a sensor configured to generate a sensor electromotive force (EMF) that measures a magnetic field that is generated by a magnetic field transmitter. The magnetic tracking device includes a mechanism configured to adjust a sensitivity of the sensor between a higher EMF state of the sensor EMF and a lower EMF state of the sensor EMF. The magnetic tracking device includes an interconnecting circuit configured generate a parasitic EMF when receiving the magnetic field. In some implementations, the interconnecting circuit is configured to connect to a processing device. The processing device is configured to receive a first measurement representing the higher EMF state of the sensor EMF and the parasitic EMF, receive a second measurement representing the lower EMF state of the sensor EMF and the parasitic EMF, compare the first measurement and the second measurement, and based on comparing the first measurement and the second measurement, determine an approximate value of the sensor EMF.

In some implementations, the mechanism comprises a ferromagnetic core disposed inside the sensor, and wherein the higher EMF state corresponds to a higher sensor sensitivity, and wherein the lower EMF state corresponds to a lower sensor sensitivity.

The details of one or more embodiments of the subject matter described herein are set forth in the accompanying drawings and the description below. Other features, objects, and advantages of the subject matter will be apparent from the description and drawings, and from the claims.

DESCRIPTION OF DRAWINGS

Like reference symbols in the various drawings indicate like elements.

DETAILED DESCRIPTION

An Electromagnetic Tracking (EMT) system (also called a magnetic tracking system) can be used in various environments, such as medical settings, to track an object (e.g., a tracked object). For example, in a surgical setting, the EMT system can be used to track medical equipment (e.g., a surgical tool) for one or more purposes (e.g., endoscopic surgery), thereby allowing the three-dimensional position (e.g., location) and the orientation of the object to be known to a medical professional (e.g., a surgeon) during a medical procedure. Generally, the magnetic tracking system is configured to track objects inside a body to assist the medical professional with an operation performed by the medical professional.

Figure 1:
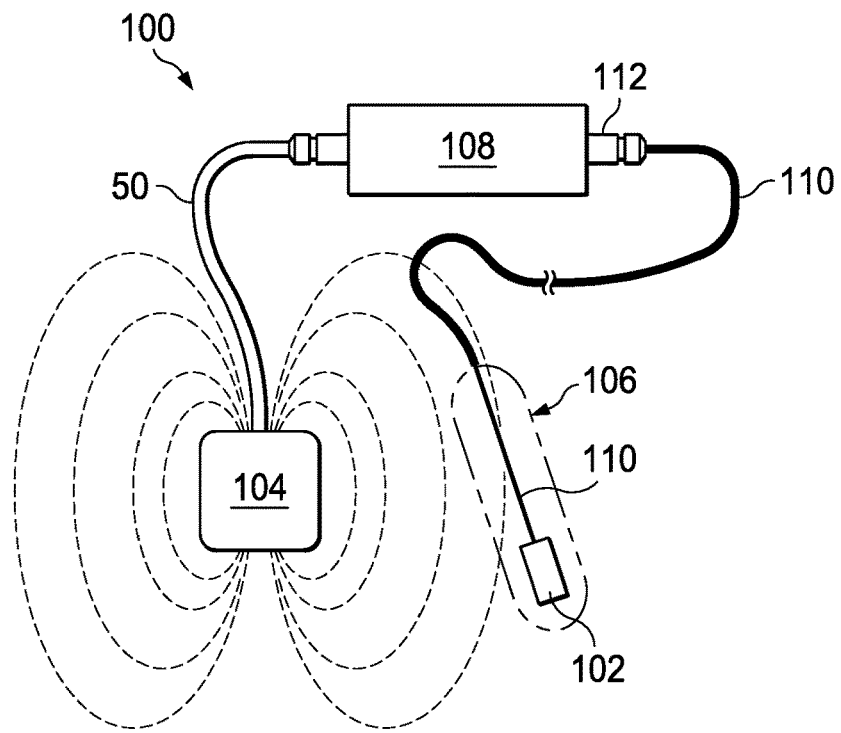
FIG. 1 shows an illustration of an example magnetic tracking system.

FIG. 1 shows an illustration of an example magnetic tracking system 100. The ideal magnetic tracking system receives 100% of its signal input exclusively from the sensor coil, where the sensor signal is a response to a transmitted time varying magnetic field. The sensor coil signal traverses the sensor assembly interconnect system travelling from the sensor coil through cable wires, to and through the connector, and through signal conditioning such as an amplifier and analog-to-digital converter mounted on a printed circuit board. The interconnect system components generate spurious signals in response to the transmitted time varying magnetic field. These spurious signals sum to corrupt the otherwise ideal sensor coil signal, and thus induce position and orientation error of the tracked instrument. The magnetic tracking system 100 is configured to reduce or eliminate these errors by isolating the EMF from the coil from EMF produced by other components of the magnetic tracking device 200 as the magnetic tracking device moves around the environment of the magnetic tracking system 100. For example, the magnetic tracking system 100 is configured to remove the spurious error-inducing signals generated within the sensor assembly interconnect, leaving the desired sensor coil signal uncorrupted.

The magnetic tracking system 100 includes a magnetic sensor 102, a magnetic transmitter 104, a computing system 108 and an instrument 106 whose position is being tracked. In some implementations, the instrument 106 can include a catheter device configured to be disposed inside a vasculature of a patient. In some implementations, the instrument 106 can include a portion of an ultrasound device. Magnetic sensor 102 is connected to a computing system 108 via cable 110 and connector 112. Magnetic transmitter 104 is connected to computing system 108 via cable 110. Magnetic sensor 102 outputs signals in response to the time derivative of magnetic fields, dH/dt, generated by the magnetic transmitter 104. The computing system 108 can include a processing device or a controller. The computing system 108 receives the output signals from the magnetic sensor 102 by way of cable 110 and connector 112 and computes the position of magnetic sensor relative to the magnetic transmitter 104.

Magnetic sensor 102 may contain one or more signal channels. In one example, a typical 6 degree of freedom magnetic tracking system may be constructed using 3 signal channels within magnetic sensor 102 combined with 3 orthogonal magnetic transmitting coils housed within transmitter 104. For better clarity in this description, a single signal channel is described, because the operation of any additional signal channel is identical.

Figure 2:
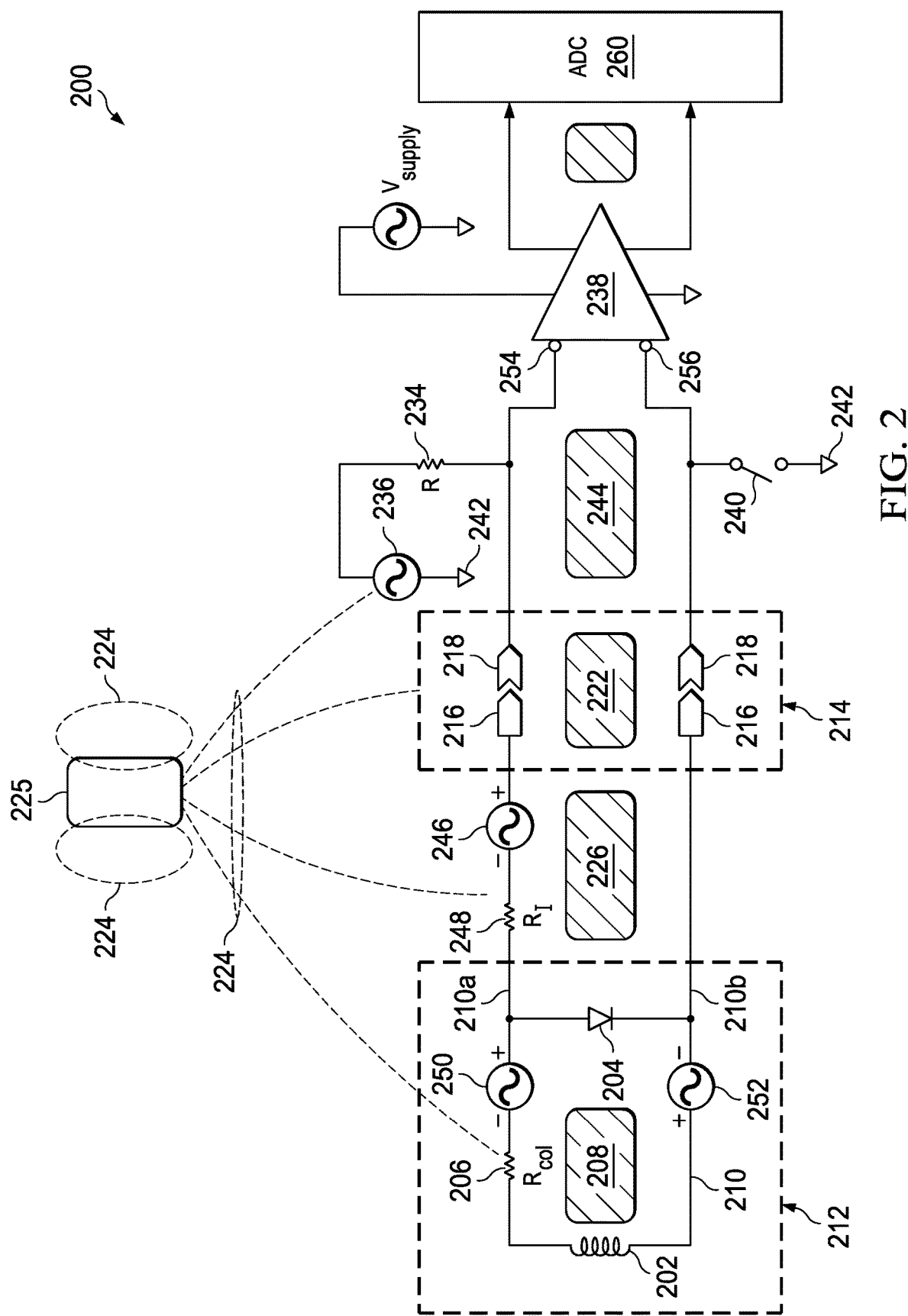
FIG. 2 shows an example schematic for a magnetic tracking device including a diode.

FIG. 2 shows an example magnetic tracking device 200, which can be a part of magnetic tracking system 100 (e.g., magnetic sensor 102). The magnetic tracking device 200 can include a magnetic sensor coil 202, a connector 214, an amplifier 238, and an analog to digital converter (ADC) 260. The coil 202 is connected to a diode 204 in parallel by interconnect conductors 210a and 210b (collectively interconnects 210). The coil 202 includes a parasitic series resistance 206 caused by finite wire conductivity. A sensor parasitic loop 208 results from the space between the diode 204 and the coil 202. Generally, the loop 208 is made as small as possible, generally under $1*e^{-6}$ square meters. The coil 202, the resistance 206, the diode 204, conductors 210, and the parasitic loop 208 are collectively referred to as magnetic sensor 212, shown by a dashed box in FIG. 2. The diode 204 can be selectively biased by a control signal to switch the magnetic sensor 212 between an ON state and an OFF state. The ON state can be called a first operating mode and the OFF state can be called a second operating mode. Switching the magnetic sensor 212 between the ON and OFF states can allow a processing device (e.g., computing system 108 of FIG. 1) to measure parasitic EMF values of the magnetic tracking device 200 that are not a result of the magnetic sensor 212 as the magnetic tracking device is positioned in or near a patient. The computing system 108 can thus subtract the parasitic EMF signal caused by portions of the magnetic tracking device 200 that are not a part of the magnetic sensor 212. This results in a more accurate position estimate for the position of the magnetic sensor 212 in an environment of the magnetic tracking system 100 of FIG. 1. The process for removing parasitic EMF values from the magnetic tracking device 200 is subsequently described in detail.

Generally, the coil 202 is configured to detect a time derivative of the magnetic field, dH/dt, generated by a transmitter 225 that is remote from the magnetic tracking device 200. The signal is sensed according to the formula shown in Equation (1):

$$EMF_{coil} = A*N*U*\frac{dH}{dt} \tag{1}$$

where A is a cross sectional area of the coil 202 in square meters, N is the number of turns in the coil 202, U is the value of free space permeability, and dH/dt is the time rate of change of the magnetic flux density, H, from the transmitter 225, in Tesla per second.

Generally, the coil 202 is ideally the only element of the magnetic tracking device 200 that is responsive to the magnetic signal 224 from the transmitter 225. Any additional signal sources between coil 202 and the ADC 260 can result in an incorrect position computation for the magnetic tracking device 200.

The magnetic tracking device 200 includes components in addition to the magnetic sensor 212. These components can introduce a parasitic EMF as previously described that results in errors in prediction of the position of the magnetic sensor 212 with respect to the transmitter 225. The magnetic sensor 212 is connected by interconnects 210 that generally run in parallel from the magnetic sensor 212 to a connector 214. As further described below, these interconnects 210 can be twisted to reduce the parasitic EMF from a loop 226 that results from the interconnects 210 running in parallel to the connector 214. The interconnects 210 include a resistance 248 and have an EMF 246 resulting from the magnetic signal 224 from the transmitter 225.

In some implementations, some systems depend upon a high quality twisted pair cable to conduct the EMF from coil 202 to connector 214. The twisted pair cable provides cancellation of magnetic signals by way of forming small opposing loops along its length, causing the EMF of each successive loop to change polarity with respect to its neighbors and thereby to cancel the effects of any external magnetic fields. This cancellation works well in a uniform magnetic field. However, in a gradient magnetic field, the dH/dt magnitude is not uniform along the cable and therefore the EMF for successive loops is not uniform. In this case, the cable can introduce a cable error, $EMF_{cable}$. $EMF_{cable}$ has the highest magnitude when the cable is placed on or near the transmitter 225, due to the high gradient field near the transmitter 225. An example of this occurrence is when instrument 106 is an ultrasound transducer and the operator inadvertently pulls the cable across the transmitter 104. Generally, the interconnect conductors 210 are typically between about 20 centimeters (cm) to 1 meter (m) long and continue to connector 214. In some implementations, the loop area 226 can be a result of a diameter of a guidewire 430 of the magnetic tracking device 200, shown in FIG. 4 and described in further detail below.

The connector 214 includes male contacts 216, female contacts 218, support material 320 (shown in FIG. 3), and parasitic loop area 222. An source of error to the EMF of the magnetic sensor 212 occurs where the signals from coil 202 pass through the connector 214. In most high density pin type connectors, the pins form a parallel path over their mating length. This path has a net area described by the product of pin length and pin separation. This net area is shown as a connector pin loop 222 in FIG. 2. The EMF from connector pin loop 222 is then described as:

$$EMF_{connector} = L_{pin} * W_{pin} * U * \frac{dH}{dt} \quad (2)$$

where $L_{pin}$ is the length of a connector pin, $W_{pin}$ is the pin separation distance, U is the free space permeability, and dH/dt is the time rate of change of the magnetic flux density, H, from transmitter 225.

Loop area 222 can be difficult to eliminate with common pin type connector contacts as they generally are straight and parallel for a finite distance, often 1 cm or more, and are separated by distances on the order of 1 millimeter (mm). In this situation, loop area 222 creates significant undesired EMF 246 on interconnects 210 when exposed to the derivate dH/dt of the transmitted magnetic field 224 generated from magnetic transmitter 225. The undesired EMF alters the signal from coil 202 which can cause errors in the reported position of coil 202. Numerous connector types possess parasitic EMF issues including PCB edge finger, co-axial (caused by conductor mis-centering and/or transmitted field gradient), insulation displacement, and Flat panel connectors (FPC).

In some implementations, the loop 222 may be located near the transmitter 225 while the coil 202 may be near the outside limits of its range. Thus the value of dH/dt at loop 222 may be orders of magnitude larger than the dH/dt at coil 202. This could occur, for example, if a catheter operator positions a computing device and the connector 214 near the transmitter 225 due to space constraints in a procedure room. Some systems commonly place a restriction on the position of the connector 214 relative to the transmitter 225, a common restriction being 0.6 meters of minimum separation. Some systems also commonly employ a magnetic shield around connector 214, to decrease the dH/dt magnitude at loop 222. Such a shield adds cost and bulk to connector 214, and can cause distortion of the magnetic field transmitted by transmitter 225 if placed too closely.

Generally, the magnetic tracking device 200 is connected to a processing device (e.g., computing system 108 of FIG. 1). The processing device is configured to receive signals from the magnetic tracking device for determining a location of the magnetic tracking device 200. For example, a sensing signal passes through the amplifier 238, then through the ADC 260 and to the processing device. Another parasitic EMF can be caused by loop area 244. The loop area 244 results from the sense nodes 256 and 254 to the amplifier 238, from the connector 214. Generally, this circuitry is for signal conditioning and for introduction of a biasing control from source 236. In some implementations, this can be a short length (e.g., a few millimeters to centimeters on a printed circuit board). The loop area 244 error is significant because circuitry used to energize transmitter 225 is contained within the computing system 108 and there is commonly some leakage dH/dt from this circuitry. To fit the computing system 108 into a small form factor, the spacing between this energizing circuitry and loop area 244 may be only a few tens of millimeters. This can result in a significant leakage dH/dt component being present, as defined in Equation (3).

$$EMF_{trace} = A_{trace} * U * \frac{dH}{dt} \quad (3)$$

where $A_{trace}$ is the trace loop area, U is the free space permeability, and dH/dt is the time rate of change of the magnetic flux density, B, from the transmitter 225. The amplifier is connected to a source voltage $V_{supply}$ and to the ADC 260.

The loop 244 is connected to ground 242 though a switch 240. The loop 244 is connected to a source signal 236 through some resistance 234. The source 236 is a biasing signal for controlling the diode 204 operation and thus for activating or deactivating the magnetic sensor 212. The magnetic tracking device 200 is configured to determine the value of $EMF_{coil}$ by measuring the EMF of the magnetic tracking device 200 when the magnetic sensor 212 is activated and again with the magnetic sensor 212 is deactivated (e.g., using diode 204).

For the purpose of circuit analysis, the undesired sum of EMF from loops 226, 222, and 244 is shown as interconnect EMF 246. Additionally, the EMF from the magnetic sensor 212 is called sensor parasitic EMF 250 or parasitic EMF 250. Thus, the interconnect EMF includes the EMF introduced not only from the interconnects 210, but also the connector 214 and the trace loops 244.

The operation of the magnetic tracking device 200 for determining the $EMF_{coil}$ is now described. The bias supply $V_{bias}$ 236 is typically chosen to center the input range of the differential amplifier 238 at approximately half of the supply voltage $V_{supply}$. The value of $V_{bias}$ is also chosen to provide an appropriate impedance to create current flow in the circuit when analog switch 240 is placed in a low impedance state for the circuit. Analog switch 240 is used to form a series pathway to reference potential 242, referred to as ground in this case. Generally, $V_{bias}$ 236, bias resistance 234, interconnect EMF 246, interconnect resistance 248, sensor parasitic loop EMF 250, coil resistance 206, coil 202, sensor coil EMF 252, and switch 240 form a series circuit Amplifier 238 measures the potential difference across sense node 256 and 254.

During sensing operation, switch 240 is open and both inputs 254, 256 to the amplifier 238 are at high impedance. A sum of coil EMF 252 (or sensor EMF 252), parasitic EMF 250 and interconnect parasitic EMF 246 are small enough not to forward bias diode 204, typically less than 0.5 volts (V) for a silicon diode. Essentially no current flows through any of the resistance elements in the circuit such that sensor parasitic EMF 250, sensor EMF 252, and interconnect EMF 246 sum algebraically and appear across amplifier inputs 254 and 256. Interconnect parasitic EMF 246 is typically orders of magnitude larger than sensor parasitic EMF 250. Thus, this EMF is accounted for to increase the accuracy of determining the position of the magnetic sensor 212 with respect to the transmitter, while the sensor parasitic EMF 250 causes a relatively small error.

To correct for the interconnect EMF 246, the following procedure can be used. The switch 240 is closed and $V_{bias}$ source 236 is commanded to output +0.5V which results in a current the series circuit previously described. The voltage at node 254 is measured. The series current in the loop is then known as $$I_{loop} = \frac{V_{bias} - V_{measured})}{R_{bias}} \quad (4)$$

Additionally, $R_{interconnect} + R_{coil} = \frac{V_{measured} \text{measured}}{I_{loop}} \quad (5)$ A measurement interval is chosen to be sufficiently long and the measurement is made with a direct current (DC) such that the induced EMF components (which are alternating current (AC) in nature) of the loop average to zero. Thus the sum of Read 206 and $R_{interconnect}$ 248 can be accurately measured. The voltage source 236 is then increased such that $I_{loop}*R_{coil}$ 206 is greater than the forward bias voltage of diode 204, typically about 0.65V. At this point the dynamic resistance of diode 204 becomes very small, typically less than 0.5 Ohms (e.g., for a typical diode).

Figure 5:
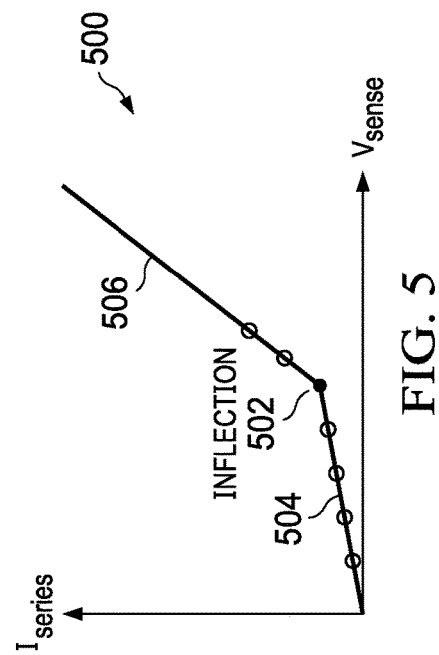
FIG. 5 shows a V/I graph.

Briefly referring to FIG. 5, a graph 500 shows the relationship for the current and the bias voltage for diode 204. A turn-on point of the diode 204 occurs at the inflection point 502 in the V/I slope graph 500. The graph 500 is generated by measuring $V_{sense}$ over a number of values for $I_{series}$. The V/I slope of line segment section 504 is the $R_{coil}+R_{interconnect}$ 248 when diode 204 is off. The slope of line segment section 506 is $R_{interconnect}+R_{diode}$ when the diode is forward biased. The point at which the slope changes is inflection point 502. This is the switching point for bypassing the magnetic sensor 212 circuit loop 208 and removing the sensor EMF 252 from the total EMF of the magnetic tracking device 200.

Returning to FIG. 2, $R_{coil}$ 206 can then be computed as $R_{coil}=R_{total}-(R_{interconnect}-R_{diode})$. Typically $R_{coil}$ and $R_{interconnect}$ are much greater than $R_{diode}$ such that small errors in diode ON resistance characteristics are not critically important and can be ignored or set to a representative fixed value, typically about 0.5 Ohm or the value indicated by the manufacturer data sheet.

Because Read and $R_{interconnect}$ are known, with diode 204 is left in the forward biased condition, the parasitic EMF 250 and Interconnect EMF 246 as induced by the operation of transmitter 225 can be measured. During this measurement, the computing system 108 is configured to switch to an AC measurement scheme when the DC component is not important. The computing system 108 is configured to synchronize the measurement of the AC signal with the operation of magnetic transmitter 225. This is accomplished by utilizing operating state of a prior art magnetic position measurement system. The computing system 108 is configured to measure the interconnect EMF 246 in isolation from sensor EMF 252 and sensor parasitic EMF 250 as these elements are effectively short circuited by the low dynamic resistance of forward biased diode 204.

We wish to account for the effects of the voltage divider formed by bias resistor 234 and interconnect resistance 248 have on this measurement, as these two elements are present during normal operation of the tracking system. During normal operation the corrected parasitic Interconnect EMF is shown by Equation (6):

$$\text{Corrected } EMF_{Interconnect} = \frac{EMF_{measured}}{R_{interconnect}/(R_{interconnect}+R_{bias})} \quad (6)$$

In other words, a change an impedance of the interconnecting circuit in the second operating mode relative to the impedance of the interconnecting circuit in the first operating mode can be determined, and the approximate value of the $EMF_{coil}$ can be adjusted as a result of the determined differences in the $EMF_{interconnect}$ in each of the two operating modes.

During operation of the magnetic tracking device 200, a corrected sensor EMF is computed by given by $EMF_{corrected}=EMF_{250}+EMF_{252}+EMF_{246}-(\text{Corrected}$ $EMF_{Interconnect})=EMF_{250}+EMF_{252}$. During a tracking operation, $EMF_{250}$ (the parasitic sensor EMF 250) is generally small compared to $EMF_{252}$ (the sensor EMF 252) and is also generated very near the sensor coil by a rigidly held conductor loop such that is has minimal effect on reported sensor position.

Thus, the corrected EMF can be determined by comparing the EMF of the magnetic tracking device 200 when the diode is in an ON state (e.g., a first operating mode of the magnetic sensor 212) to the EMF of the magnetic tracking device when the diode is in the OFF state (e.g., a second operating mode of the magnetic sensor 212). To perform a measurement cycle, the computing system 108 can be configured to switch the diode to an ON state using $V_{bias}$ 236, measure the EMF of the magnetic tracking device 200, switch the diode to the OFF state, again measure the EMF of the magnetic tracking device, and compare the two measurements. A cycle can be performed to synchronize with the transmitter 225, as previously described, so that as the magnetic tracking device 200 is moved around, an accurate position estimate can be provided. In some implementations, a longer measurement cycle can be used, such as if the magnetic tracking device 200 is stationary with respect to the magnetic signal transmitter 225.

Generally, the diode 204 is placed as close as possible to the coil 202 to minimize the effects of the loop 208 on the sensor signal. Generally, the size of the loop 208 can be about $1e^{-6}$ m$^2$.

The process shown above reduces or eliminates a need to shield the interconnect loop 226, connector 214, or trace loops 244 to reduce the interconnect EMF 246. This can reduce the cost of manufacture of the magnetic tracking device 200, which is intended to be disposable and low cost. Additionally, as described in relation to FIG. 4 below, the interconnects 210 need not be twisted to reduce interconnect EMF 246, reducing a cross section of a guidewire for the magnetic tracking device 200, such as when the magnetic tracking device 200 is inside a catheter or other instrument inside a patient.

Figure 3:
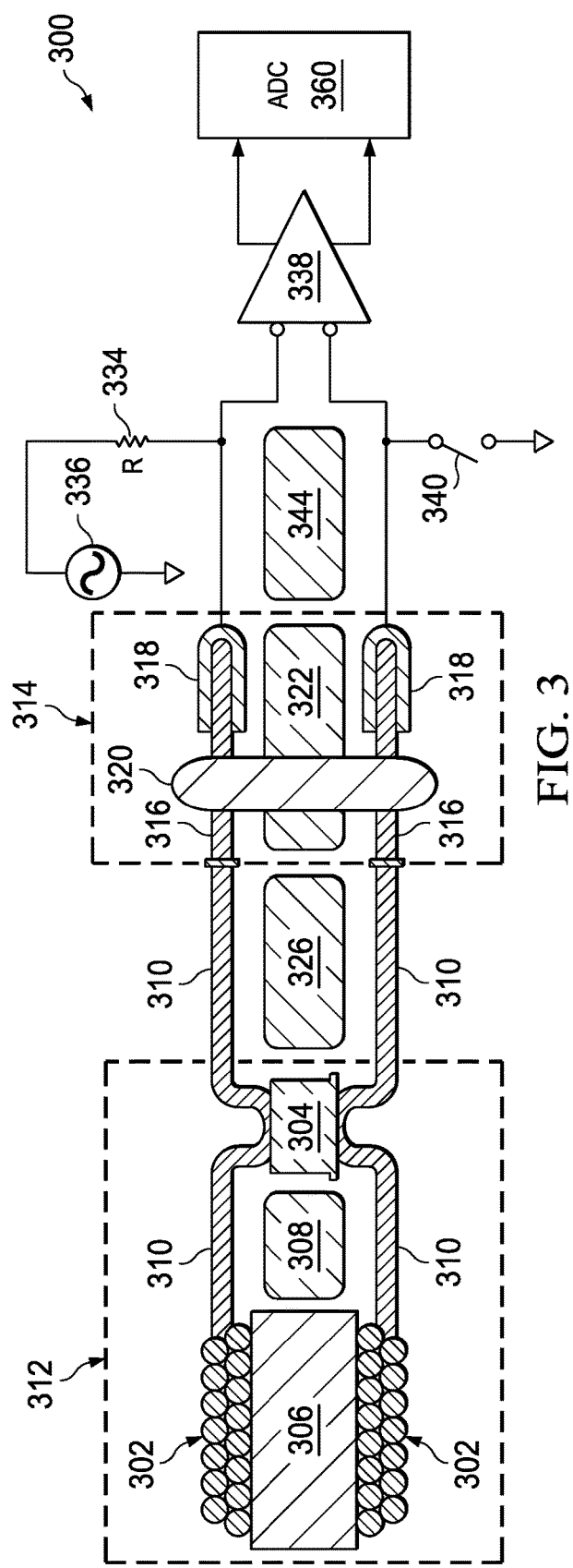
FIG. 3 shows a physical representation of the magnetic tracking device of FIG. 2.

FIG. 3 shows a physical representation of a magnetic tracking device 300, such as magnetic tracking device 200 of FIG. 2. The coils 302 (similar to coil 202) are shown around a core 306. The interconnects 310 connected the magnetic sensor 312 (e.g., similar to magnetic sensor 212) to the connector 314 (similar to connector 214). A diode 304 (similar to diode 204) can be used to turn the magnetic sensor 312 ON and OFF for measurement of the EMF values for the magnetic tracking device 300. Interconnect parasitic loop 326 is shown between interconnects 310, and is similar to loop 226. A support material 320 is a part of connector 314 for connecting male contacts 316 and female contacts 318, respectively. A $V_{bias}$ source 336 and resistor 334 are connected to the interconnects 310, and a switch 340 connects the interconnects 310 to ground. An amplifier 338 (similar to amplifier 238) is connected to ADC 360 for sending EMF signals to the processing device (not shown).

Figure 4:
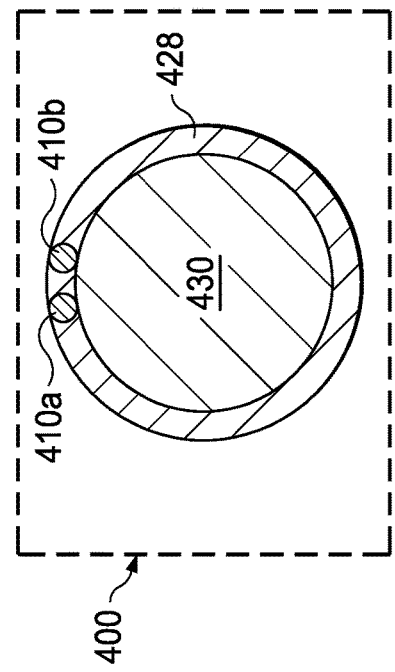
FIG. 4 shows a cross section of a guide wire.

FIG. 4 shows a cross section of a guidewire 400 for connecting a magnetic sensor (e.g., magnetic sensor 212) to a connector (e.g., connector 214), such as when the magnetic tracking device 200 is in a catheter or otherwise configured to be placed inside a patient. Interconnects 410a-b (similar to interconnects 210) provide two paths for the current to pass into and out of the magnetic sensor 212, as previously described. The two interconnects 410a-b (collectively interconnects 410) create an interconnect loop area (e.g., loop 226 of FIG. 2) because the interconnects run in parallel to one another. Generally, an outer diameter 428 of the guidewire 400 is made as small as possible, commonly 0.4 mm or less, and circular in cross section. This geometry is configured to allow the guidewire to navigate through anatomy of a patient, and for the wire to rotate and curve as needed. Internal to the guidewire 400 is a metal core 430 which is large enough to possess column strength to allow the guidewire 400 to be pushed through the vascular anatomy.

In general, the outer diameter 428 is made as small as possible, and the distance between the outer diameter and the core 430 is made as small as possible. Because the interconnect conductors 410 reside in the space between the outer diameter 428 and the core 430, the spacing is large enough to accommodate at least one diameter of an interconnect 410. Generally, to reduce the effects of the interconnect loop EMF 226 of FIG. 2, the interconnects 210 can be twisted together to create many smaller loops in reverse configurations, of which the net EMF cancels out. However, because the magnetic tracking device 200 is already configured to correct for the interconnect EMF 246, the interconnects 410 need not be twisted together. This reduces the space between the outer diameter 428 and the core 430 by at least half, as twisting the interconnects 410a and 410b requires a space of at least two diameters of the interconnects 410. Thus, the diameter of the guidewire 400 can be made smaller because the need to twist the interconnects 410a and 410b to reduce the interconnect EMF is reduced or eliminated, as the interconnect EMF is no longer a source of error.

Generally, while diode 204 is used as a switching element for magnetic tracking device 200, any device can be used that is configured to switch the magnetic sensor 212 between an ON state in which current is flowing through the coils 202 and an OFF state in which no current is flowing through the coils. For example, switch can be a relay, a field effect transistor (FET), and so forth.

Figure 6:
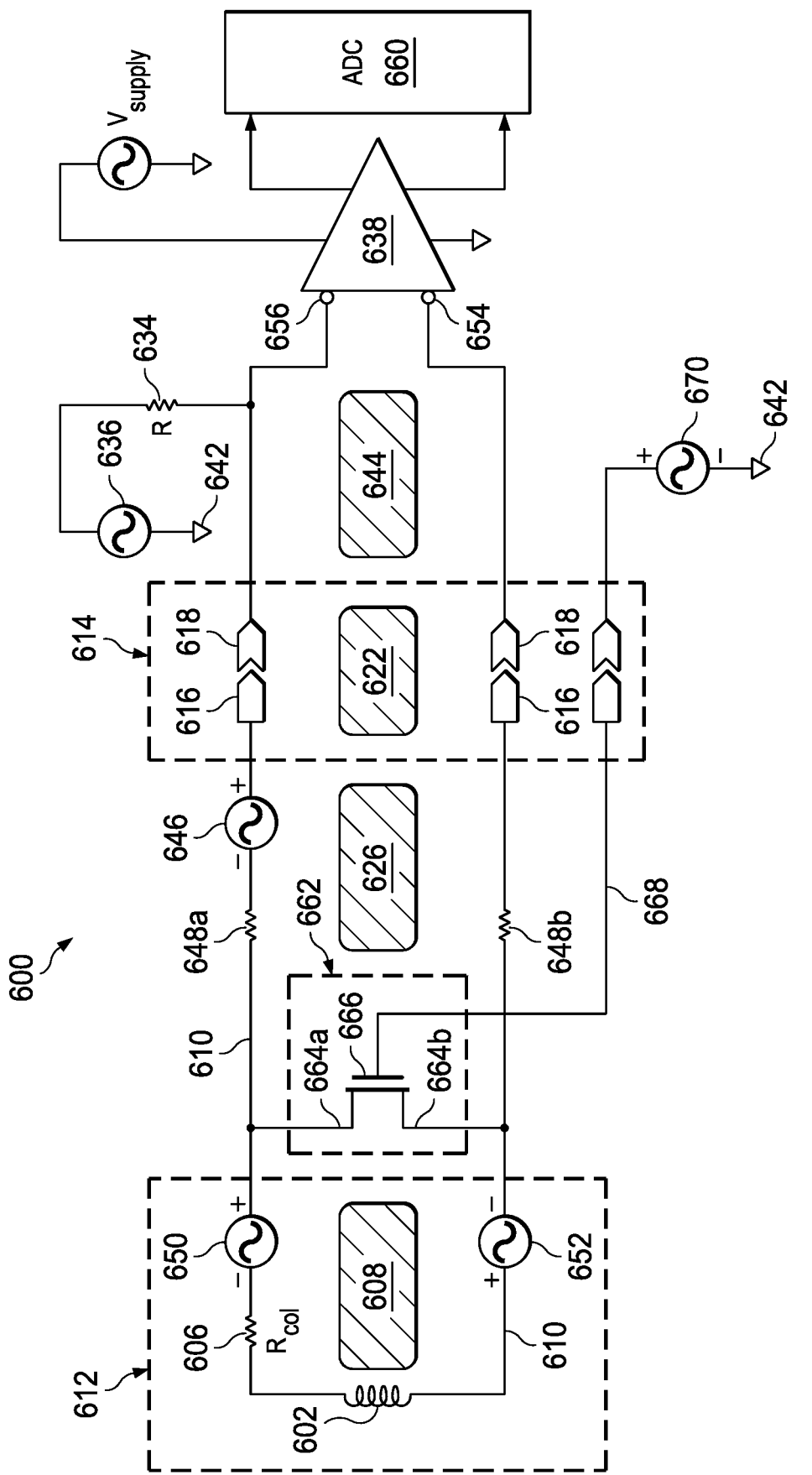
FIG. 6 shows an example schematic for a magnetic tracking device including a switching device.

FIG. 6 shows an example of a magnetic tracking device 600 that is similar in operation to the magnetic tracking device 200 of FIG. 2. A switching device 666 replaces the diode 204. As previously described, the switching device 666 may include devices from a list including of junction gate field-effect transistor (JFET), metal-oxide-semiconductor field-effect transistor (MOSFET), bipolar transistor, or relay, or a similar switching device. Generally, the switching device 666 includes terminals 664 and an open/close control 662. When the magnetic tracking device 600 is configured to operate in a position tracking mode (e.g., by a processing device, not shown), the control 662 is configured to cause the switching device 666 to be open 664. The open mode for the switching device 666 is such that there is high impedance between the terminals 664a and 664b (collectively terminals 664). The magnetic sensor 612 operates similar to magnetic sensor 212, in which current on interconnects 610 through resistor 606 and coil 602 generates a coil EMF 652. A parasitic sensor EMF 650 is also generated, as previously described. The processing device configures the magnetic tracking device 600 for measuring the interconnect EMF 646, which includes EMFs from loops 626, 622, and 644. The control 662 is configured to cause a low impedance (ideally about 0.5 ohms or less) between terminals 664a and 664b.

Similar to magnetic tracking device 200, a connector 614 includes male contacts 616 and female contacts 618, the geometry of which generates a connector EMF from loop 622. The interconnects 610a and 610b, each having a respective resistance 648a-b, form a loop 626 which generates a portion of the interconnect EMF. The amplifier 638 includes terminals 656 and 654 for connecting to the interconnects 610a-b and creates a loop 644 which is a part of the interconnect EMF 646. Similar to magnetic tracking device 200, a bias voltage source 636 can be used to provide current to the magnetic sensor 212 through resistor 634, where potential 642 represents ground. An ADC 660 receives signals from the amplifier 638.

The control 662 can include one or more control signals or circuitry necessary to operate the switching device 666 and toggle the device between a first operating mode of the magnetic tracking device 600 (e.g., an ON state of the magnetic sensor 612) and a second operating mode (e.g., an OFF state of the magnetic sensor). In the low impedance state (e.g., the second operating mode), the switching device 666 behaves in a functionally similar manner to the diode 204 when the diode is in the forward biased state. In the case where switching device 666 is a voltage controlled device, such as a MOSFET (shown in FIG. 6), the operation of the preferred embodiment can be simplified at the expense of an additional conductor 668. During normal operation (e.g., the first operating mode), control voltage 670 is below a turn-on voltage of the MOSFET and there is high impedance between the terminals 664a, 664b. Essentially no current flows through any of the resistance elements in the circuit such that sensor parasitic EMF 650, sensor EMF 652, and interconnect EMF 648 sum algebraically and appear across amplifier inputs 654 and 656.

To eliminate interconnect parasitic EMF 646, as it is typically orders of magnitude larger than sensor parasitic EMF 650, the following procedure can be used by the processing device (e.g., computing system 108). A control voltage 670 is set to a level sufficient to turn on the switching device 666 (e.g., a MOSFET), typically about 3 Volts in this example. In this example, due to the MOSFET being a purely voltage controlled device having high impedance between gate terminal (e.g., control 662) and terminals 664a, 664b, this action does not require current to flow through resistive elements 648a-b or 634 or otherwise require actions which change the impedance seen looking from terminals 664a-b into amplifier 638. Bias supply $V_{bias}$ 636 is typically chosen to center the input range of the differential amplifier 638 at approximately half of the supply voltage $V_{supply}$.

The computing system 108 is configured to measure the parasitic EMF 650 and Interconnect EMF 646 as induced by the operation of the transmitter (not shown). During this measurement, an AC measurement scheme can be utilized. In particular, the measurement of the AC signal is synchronized with the operation of magnetic transmitter, as previously described in relation to FIG. 2. The processor is able to measure the interconnect EMF 646 in isolation from sensor EMF 652 and sensor parasitic EMF 650 as these elements are effectively short circuited by the low dynamic resistance of the switching device 666 (e.g., the MOSFET). Because the impedance of the amplifier bias network is constant during both the operating mode and EMF measurement mode, the parasitic EMF 650 measurement can be subtracted directly from the total EMF during the operating mode without further correction. This may be advantageous as it utilizes fewer measurement steps and reduces the current demand on the power supplies, which for wireless devices may consist of a small coin cell battery.

Figure 7:
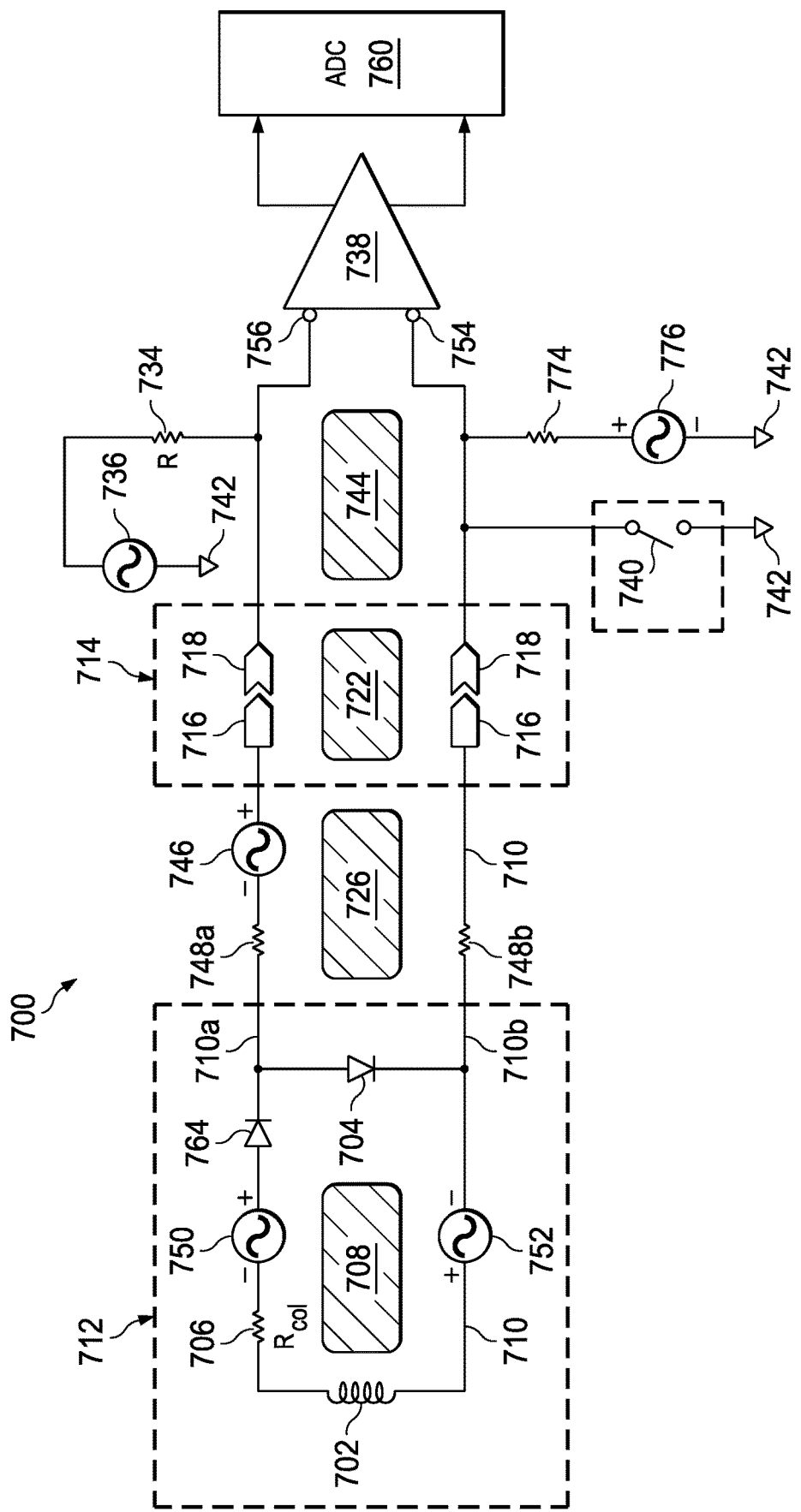
FIG. 7 shows an example schematic for a magnetic tracking device including two diodes.

FIG. 7 shows an example of a magnetic tracking device 700. The magnetic tracking device 700 includes a magnetic sensor 712. Magnetic sensor 712 includes a first diode 704 (similar to diode 204 of FIG. 2) and a second diode 764. Similar to magnetic sensor 212, magnetic sensor 712 includes a coil 702, and parasitic series resistance 706 caused by finite wire conductivity of the interconnect 710*a*, 710*b* (collectively interconnects 710). Sensor parasitic loop 708 results from the space between the diode 704, series diode 764, and coil 702 and is made as small as possible, generally under 1e$^{-6}$ square meters. In other words, coil 702, resistance 706, diode 704, series diode 764, interconnect conductors 710, and parasitic loop 708 are collectively referred to as magnetic sensor 712.

Similar to the interconnects 210*a-b*, the interconnect conductors 710 are typically 20 cm to 1 meter long and continue to connector 714. The connector 714 consists of male contacts 716, female contacts 718, support material (not shown), and parasitic loop area 722. Loop area 722 results in an EMF that is difficult to eliminate with common pin type connector contacts as they must remain straight and parallel for a finite distance, often 1 cm or more, and are separated by distances on the order of 1 mm.

The interconnects 710*a* and 710*b*, each having a respective resistance 748*a-b*, form a loop 726 which generates a portion of the interconnect EMF. The amplifier 738 includes terminals 756 and 754 for connecting to the interconnects 710*a-b* and creates a loop 744 which is a part of the interconnect EMF 746. Similar to magnetic tracking device 200, a bias voltage source 736 can be used to provide current to the magnetic sensor 712 through resistor 734, where potential 742 represents ground. An ADC 760 receives signals from the amplifier 638. A switch 740 can connect the interconnect 710*b* to ground 742. For the purpose of circuit analysis, the undesired sum of EMF from loops 708, 726, and 744 are represented as interconnect EMF 746 and the parasitic EMF from sensor 712 as sensor parasitic EMF 750. A second bias supply 776 is connected to the interconnects 710 through resistor 774.

Bias supply $V_{bias}$ 736 is typically chosen to center the input range of the differential amplifier 738 at approximately half of the supply voltage $V_{supply}$. The forward bias supply 776 and resistance 774 are chosen to forward bias diode 764. This is configured to place diode 764 in a low differential impedance state, typically 1 Ohm or less at 0.65V forward voltage and 1 mA current.

Here, $V_{bias}$ 736, bias resistor 764, the interconnect EMF 746, interconnect resistance 748, sensor parasitic loop EMF 750, coil resistance 706, coil 702, sensor coil EMF 752, diode 764, and bias resistor 774 form a series circuit. The differential amplifier 738 measures the potential difference across sense nodes 754 and 756.

During operation where the sensor coil 702 is being tracked for position, the switch 740 is open and both inputs to difference amplifier 754, 756 are high impedance. The sum of the sensor EMF 752, parasitic EMF 750, and interconnect parasitic EMF 746 are small enough not to forward bias diode 764, typically less than 100 mV for a typical total EMF. The small EMF values are also small enough not to affect the forward biased condition of series diode 764. The sensor parasitic EMF 750, sensor EMF 752, and interconnect EMF 746 sum algebraically and are multiplied by the voltage divider ratio as previously described in relation to FIG. 2, and the resulting EMF appears across amplifier inputs 756 and 754. The interconnect parasitic EMF 746 is typically orders of magnitude larger than sensor parasitic EMF 750, and thus determining what this value is (so that the position estimate of the sensor 712 can be adjusted) is performed.

The interconnect 746 is determined and the position of the sensor coil 702 is accomplished according to the following procedure. The switch 740 is closed and $V_{bias}$ source 736 is commanded (e.g., by a processing device, not shown) to output+0.5V causing to flow in the series circuit previously described. This is the first operational state in which the coil 702 is essentially ON. The voltage at node 756 of the amplifier 738 is then measured. The series current in the loop is then known as $I_{loop}=(V_{source}-V_{measured})/R_{bias}$. The sum of $R_{interconnect}+R_{coil}=V_{measured}/I_{loop}$. The measurement interval is chosen to be sufficiently long and the measurement is made at DC such that the induced EMF components (being AC in nature) of the loop average to zero and the sum of resistance 706 and resistance 748*a-b* can be accurately measured. Next, voltage source 736 is increased such that $I_{loop}*R_{coil}$ 706 is greater than the forward bias voltage of diode 704, typically about 0.65V. At this point the dynamic resistance of diode 704 becomes very small, typically less than 0.5 Ohms. This is the second operating mode of magnetic tracking device 700 in which the coil is essentially OFF.

With $R_{coil}$ and $R_{interconnect}$ known, and with diode 704 left in the forward biased condition, the processor configures the circuit for measuring the parasitic EMF 750 and $EMF_{interconnect}$ 746 as induced by the operation of a magnetic signal transmitter (not shown). During this measurement, the circuit is switched to an AC measurement scheme when the DC component is not important. In particular the processor is configured to synchronize the measurement of the AC signal with the operation of magnetic transmitter. The processing device measures the interconnect EMF 746 in isolation from sensor EMF 752 and sensor parasitic EMF 750 as these elements are effectively short circuited by the low dynamic resistance of forward biased diode 704.

To account for the effects the voltage divider formed by bias resistor 734 and interconnect resistance 748*a-b* have on this measurement, as these two elements are present during normal operation of the tracking system, a corrected parasitic Interconnect EMF is determined. The corrected parasitic interconnect $EMF=EMF_{measured}/(R_{interconnect}/(R_{interconnect}+R_{bias}))$, similar to the process described previously with respect to FIG. 2. During EM operation, the processing device is configured to compute a corrected sensor EMF given by $EMF_{conected}=EMF_{750}+EMF_{752}+EMF_{748}-$(corrected parasitic EMF)$=EMF_{750}+EMF_{752}$. During normal tracking operation, parasitic sensor $EMF_{750}$ is generally small compared to sensor $EMF_{752}$ and is also generated very near the sensor coil by a rigidly held conductor loop such that is has minimal effect on reported sensor position. In other words, a change an impedance of the interconnecting circuit in the second operating mode relative to the impedance of the interconnecting circuit in the first operating mode can be determined, and the approximate value of the $EMF_{coil}$ can be adjusted as a result.

Figure 8:
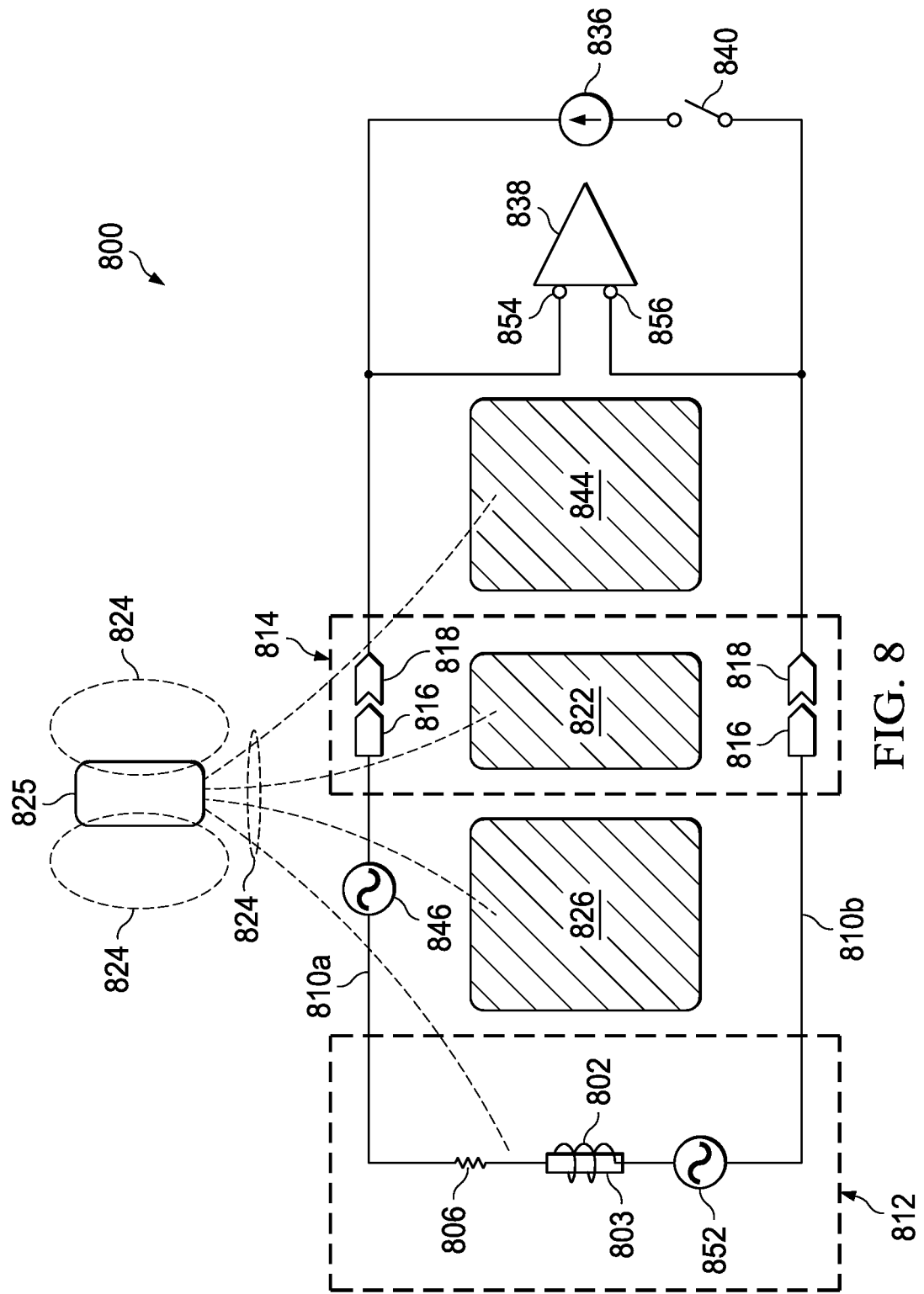
FIG. 8 shows an example of a schematic for a magnetic tracking device.

FIG. 8 shows an example magnetic tracking device 800. The magnetic tracking device 800 includes a magnetic sensor 812 including coils 802 having a ferromagnetic core 803. The core 803 can be a ferromagnetic core that is used to increase the EMF produced by the coils 802 when experiencing a magnetic field from the transmitter 825. The induced EMF of the sensor coil (e.g., $EMF_{coil}$) is shown in Equation (7):

The induced EMF 26 into a sensor coil is:

$$EMF = \mu 0 * \mu r * N * A * \frac{dH}{dt} \qquad (7)$$

where µ0 is the permeability constant, µr is relative permeability of the sensor core 803, N is number of turns of the coil, A is the cross section of the coils 802, and dH/dt the field strength to be measured.

Magnetic tracking device 800 can be similar in many respects to the magnetic tracking devices previously described. A magnetic sensor 812 is connected to conductive interconnects 810a-b (collectively interconnects 810). A connector 814 connects the magnetic sensor 812 to a differential amplifier 838 for sensing the magnetic sensor 812 signal (e.g., the $EMF_{sensor}$). A source 836 provides a current through the magnetic sensor 812, and can be turned on or off by switch 840 for switching on the operation of the magnetic tracking device 800. Additionally, a magnetic signal transmitter 825 generates a magnetic field 824, which is sensed by coils 802 of the magnetic sensor and causes an EMF 852 response in the coils. The differential amplifier senses the EMF generated by the magnetic sensor 812 at leads 854 and 856. FIG. 8 also shows a resistor 806 representing the inherent resistance of the wire in the magnetic sensor 812.

Three loops are created by this circuit, including interconnect loop 826, connector loop 822, and trace loop 844. Each of these loops can generate a parasitic EMF signal during operation of the magnetic tracking device 800, similarly to the parasitic EMFs described previously in relation to magnetic tracking devices 200, 600 and 700. This total parasitic EMF is referred to as $EMF_{interconnect}$ 846.

The magnetic tracking device 800 is different from magnetic tracking devices 200, 600, and 700 previously described because it includes the ferromagnetic core 803. The magnetic tracking device 800 does not have a switching device, such as device 666, diode 204, or other device such as a MOSFET or relay.

To determine the $EMF_{sensor}$ 852, the following process can be used. A first measurement $M_1$ includes turning on the current source 836 by closing switch 840. The current is large enough in value (e.g., 1 milliamp or more), that the sensor core 803 experiences a change permeability, generally a decrease in the permeability value. The relative permeability lar of the core is different than in the prior operating state. In some implementations, the core 803 may become magnetized by a current pulse which may then be removed, with the core remaining in the differing permeability state. In a second measurement $M_2$, the current source is switched off. Then $EMF_{sensor}$ 852 of $M_2$ is µr times greater than $EMF_{sensor}$ $M_1$. The measurements are done in AC mode because the DC component (e.g., resistor 806*the current value from current source 836) is not needed for determining the $EMF_{sensor}$ 852. The difference is calculated as shown:

$$M_2-M_1=(EMF_{interconnect}\ 846+EMF_{sensor}\ 852\_M_2)-(EMF_{interconnect}\ 846+EMF_{sensor}\ 852\_M_1)=EMF_{sensor}\ 852\_M_2-EMF_{sensor}\ 852\_M_1.$$

The parasitic $EMF_{interconnect}$ 846 is thus removed. Because the ratio $EMF_{sensor}$ 852_$M_2$/$EMF_{sensor}$ 852_$M_1$=µr, all values from $M_1$ and $M_2$ can be determined when µr is known. While this particular example uses a ferromagnetic core 803, in general, the described parasitic loop compensation can be achieved with any method which changes sensitivity of the sensor 812. This is because the $EMF_{interconnect}$ 846 remains the same across $M_1$ and $M_2$.

Figure 9:
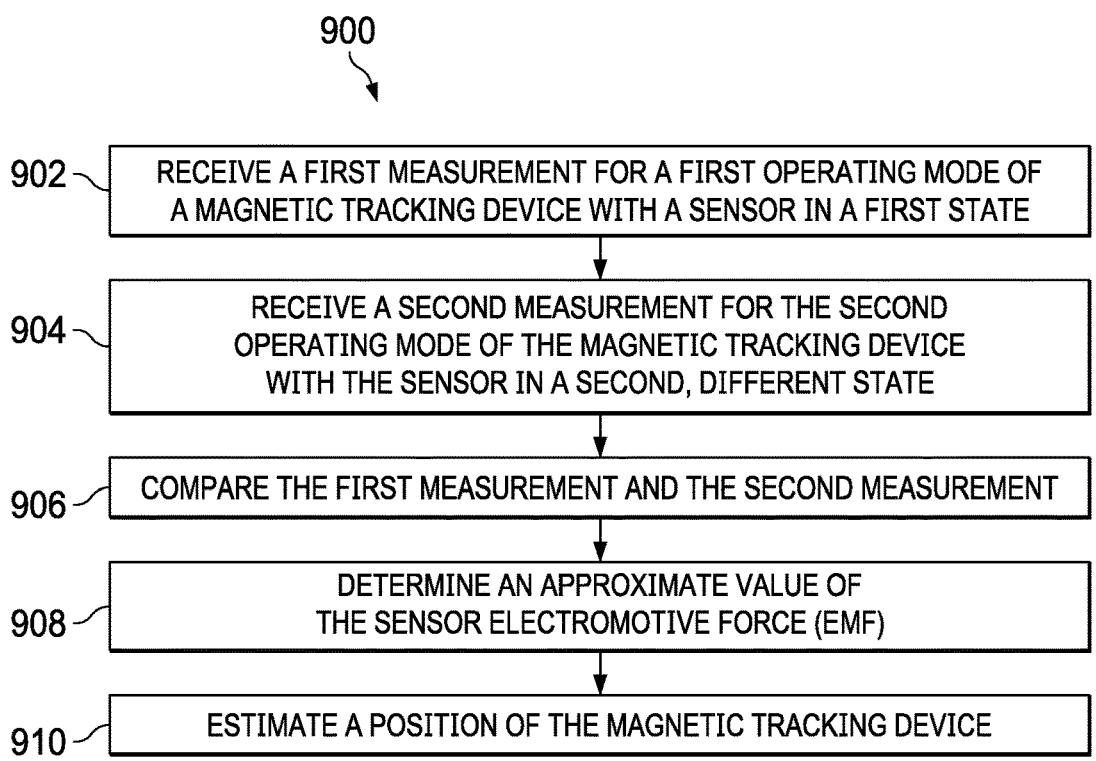
FIG. 9 shows an example flow diagram for operating a magnetic tracking device.

FIG. 9 shows an example of a process 900 for controlling a magnetic tracking device (e.g., magnetic tracking device 200, 600, 700, 800, etc.) for sensor parasitic loop compensation of the magnetic tracking device. The process includes determining, by a processing device (e.g., of computing device 108 of FIG. 1), an approximate value of a sensor EMF of the magnetic tracking device. To determine the sensor EMF, the processing device is configured to receive (902) a first measurement for a first operating mode of a magnetic tracking device with a sensor in a first state. In some implementations, the first operating mode can include an ON state or activated state of the magnetic sensor (e.g., magnetic sensor 212, 612, 712, etc.). In some implementations, the first operating mode comprises a high sensitivity state of the magnetic sensor (e.g., magnetic sensor 812). In some implementations, the processing device can control a switching device or other mechanism, such as biasing a diode, to control the magnetic tracking device to be in the first operating state.

The process 900 includes receiving (904) a second measurement for the second operating mode of the magnetic tracking device with the sensor in a second, different state. In some implementations, the second operating mode can include an OFF state or deactivated state of the magnetic sensor (e.g., magnetic sensor 212, 612, 712, etc.), such that the sensor coil EMF is reduced or changed. In some implementations, the second operating mode comprises a low sensitivity state of the magnetic sensor (e.g., magnetic sensor 812). In some implementations, the processing device can control a switching device or other mechanism, such as biasing a diode or setting a current to the sensing coil, to control the magnetic tracking device to be in the second operating state.

The process 900 comprises comparing (906) the first measurement and the second measurement. Comparing the first measurement and the second measurement can include comparing EMF values measured by the processing device, such as using a differential amplifier, in each operating mode of the magnetic tracking device. In some implementations, an adjustment can be made to account for a change in impedance in a portion of the magnetic tracking device when changing the modes for the comparison.

The process 900 includes determining (908) an approximate value of the sensor electromotive force (EMF) of the magnetic sensor of the magnetic tracking device. The approximate value is based on the comparison. In some implementations, the processor uses the approximate value of the sensor EMF to estimate (910) a position of the magnetic tracking device, such as a position relative to a magnetic signal transmitter. In some implementations, the magnetic tracking device is inside a patient or near a patient during the process 900.

Figure 10:
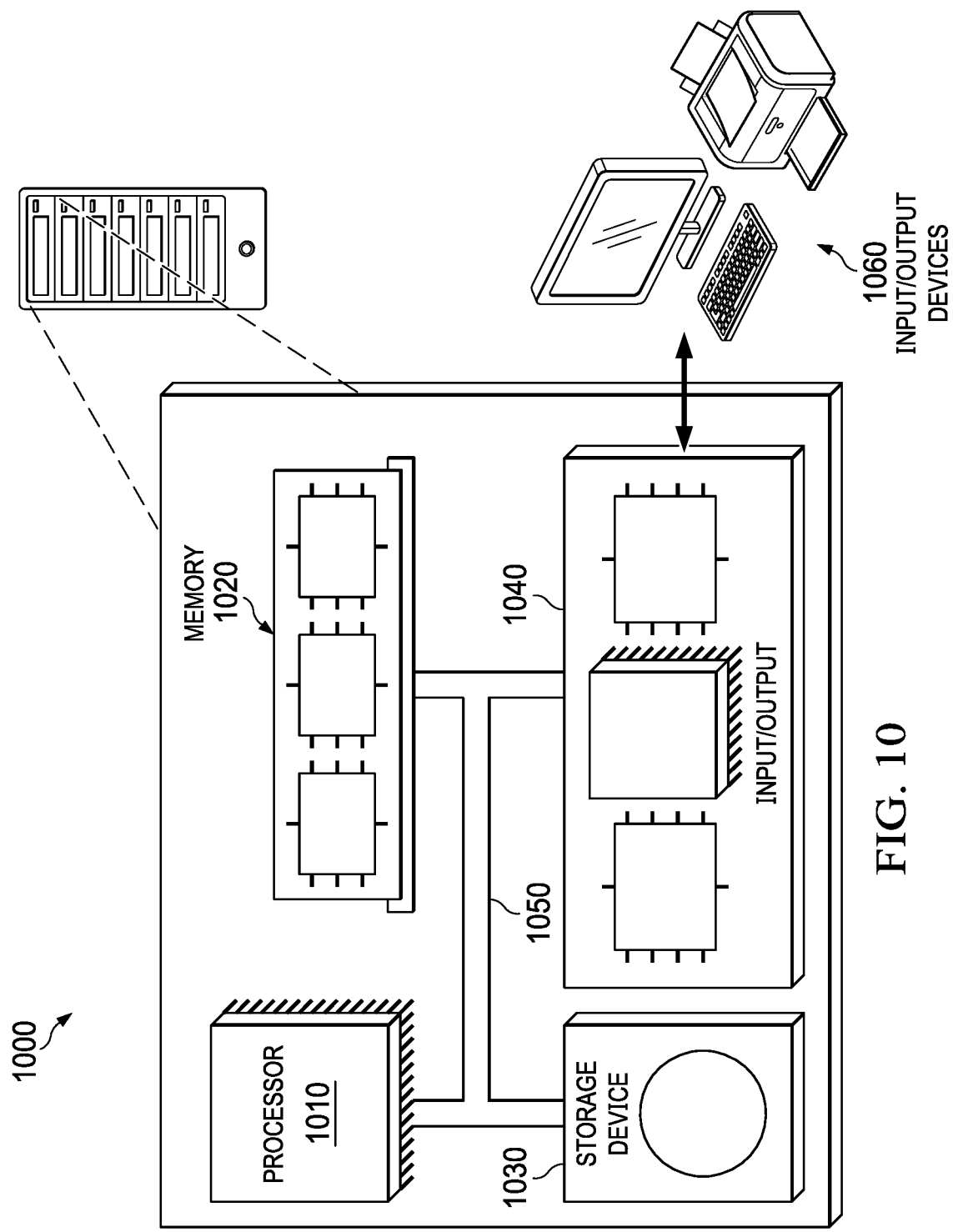
FIG. 10 is a block diagram of an example computer system.

FIG. 10 is a block diagram of an example computer system 1000. The computing system 108 described in relation to FIGS. 1-9 may be an example of the computer system 1000 described here. The system 1000 can include a processor 1010, a memory 1020, a storage device 1030, and an input/output device 1040. Each of the components 1010, 1020, 1030, and 1040 can be interconnected, for example, using a system bus 1050. The processor 1010 is capable of processing instructions for execution within the system 1000. The processor 1010 can be a single-threaded processor, a multi-threaded processor, or a quantum computer. The processor 1010 is capable of processing instructions stored in the memory 1020 or on the storage device 1030. The processor 1010 may execute operations such as causing the magnetic tracking system 100 to determine the position and/or the orientation of tracked device 200, 300, 600, 700, etc.

The memory 1020 stores information within the system 1000. In some implementations, the memory 1020 is a computer-readable medium. The memory 1020 can, for example, be a volatile memory unit or a non-volatile memory unit.

The storage device 1030 is capable of providing mass storage for the system 1000. In an aspect, the storage device 1030 is a non-transitory computer-readable medium. The storage device 1030 can include, for example, a hard disk device, an optical disk device, a solid-date drive, a flash drive, magnetic tape, or some other large capacity storage device. The storage device 1030 may alternatively be a cloud storage device, e.g., a logical storage device including multiple physical storage devices distributed on a network and accessed using a network. In some implementations, the information stored on the memory 1020 can also or instead be stored on the storage device 1030.

The input/output device 1040 provides input/output operations for the system 1000. In some examples, the input/output device 1040 includes one or more of network interface devices (e.g., an Ethernet card), a serial communication device (e.g., an RS-232 10 port), and/or a wireless interface device (e.g., a short-range wireless communication device, an 602.11 card, a 3G wireless modem, or a 4G wireless modem). Generally, the input/output device 1040 includes driver devices configured to receive input data and send output data to other input/output devices, e.g., a keyboard, a printer, and display devices. In some implementations, mobile computing devices, mobile communication devices, and other devices are used.

The system 1000 can include a microcontroller. A microcontroller is a device that contains multiple elements of a computer system in a single electronics package. For example, the single electronics package could contain the processor 1010, the memory 1020, the storage device 1030, and input/output devices 1040.

Although an example computer system has been described in FIG. 10, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "computer system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

A number of embodiments have been described. Nevertheless, it will be understood that various modifications may be made without departing from the spirit and scope of the subject matter described herein. Other such embodiments are within the scope of the following claims.

What is claimed is:

1. A magnetic tracking device, comprising:
   a sensor configured to generate a sensor electromotive force (EMF) that measures a magnetic field that is generated by a magnetic field transmitter;
   a processing device configured to select between a first operating mode in which the sensor generates the sensor EMF when receiving the magnetic field and a second operating mode in which the sensor generates a reduced sensor EMF when receiving the magnetic field,
   a switching device in parallel with the sensor, the switching device configured to be in a high impedance state in the first operating mode and configured to be in a low impedance state in the second operating mode;
   an interconnecting circuit configured generate a parasitic EMF in each of the first operating mode and the second operating mode when receiving the magnetic field;
   wherein the interconnecting circuit is configured to connect to the processing device, the processing device further configured to:
      receive a first measurement for the first operating mode, the first measurement representing the sensor EMF and the parasitic EMF;
      receive a second measurement for the second operating mode, the second measurement representing the parasitic EMF and the reduced sensor EMF;
      compare the first measurement and the second measurement; and
      based on comparing the first measurement and the second measurement, determine an approximate value of the sensor EMF.

2. The magnetic tracking device of claim 1, wherein the switching device comprises one of a junction gate field-effect transistor (JFET), metal-oxide-semiconductor field-effect transistor (MOSFET), a bipolar transistor, or a relay.

3. The magnetic tracking device of claim 1, further comprising a diode in series with the sensor, wherein the diode is configured to be forward biased in the first operating mode and configured to be reverse biased in the second operating mode.

4. The magnetic tracking device of claim 1, wherein comparing the first measurement and the second measurement comprises:
   determining a change an impedance of the interconnecting circuit in the second operating mode relative to the impedance of the interconnecting circuit in the first operating mode; and
   based on the determining, adjusting the approximate value of the sensor EMF.

5. The magnetic tracking device of claim 1, wherein the processing device is further configured to determine an approximate position of the sensor relative to the magnetic field transmitter based on the approximate value of the sensor EMF.

6. The magnetic tracking device of claim 1, wherein the parasitic EMF comprises induced EMF values from an interconnect loop of the interconnecting circuit, a connector loop of the interconnecting circuit, a trace loop of the interconnecting circuit, or any combination thereof.

7. The magnetic tracking device of claim 1, further comprising a connector configured to connect the sensor to the processing device, the connector being a portion of the interconnecting circuit.

8. The magnetic tracking device of claim 1, wherein the processing device is configured to cause the switching device to cycle the sensor between the first operating mode and the second operating mode in synchronization with a cycle of the magnetic field that is generated by the magnetic field transmitter.

9. A magnetic tracking device, comprising:
   a sensor configured to generate a sensor electromotive force (EMF) that measures a magnetic field that is generated by a magnetic field transmitter;
   a processing device configured to select between a first operating mode in which the sensor generates the sensor EMF when receiving the magnetic field and a second operating mode in which the sensor generates a reduced sensor EMF when receiving the magnetic field,
   an interconnecting circuit configured generate a parasitic EMF in each of the first operating mode and the second operating mode when receiving the magnetic field;
   wherein the interconnecting circuit is configured to connect to the processing device, the processing device configured to:
      receive a first measurement for the first operating mode, the first measurement representing the sensor EMF and the parasitic EMF;
      receive a second measurement for the second operating mode, the second measurement representing the parasitic EMF and the reduced sensor EMF;
      compare the first measurement and the second measurement, wherein comparing the first measurement and the second measurement comprises determining a change an impedance of the interconnecting circuit in the second operating mode relative to the impedance of the interconnecting circuit in the first operating mode; and
      based on comparing the first measurement and the second measurement, determine an approximate value of the sensor EMF.

10. The magnetic tracking device of claim 9, wherein the second operating mode comprises a direct current (DC) component having a value that exceeds a threshold value to saturate a core of the sensor.

11. The magnetic tracking device of claim 9, wherein the processing device is further configured to determine an approximate position of the sensor relative to the magnetic field transmitter based on the approximate value of the sensor EMF.

12. The magnetic tracking device of claim 9, wherein the parasitic EMF comprises induced EMF values from an interconnect loop of the interconnecting circuit, a connector loop of the interconnecting circuit, a trace loop of the interconnecting circuit, or any combination thereof.

13. The magnetic tracking device of claim 9, further comprising a connector configured to connect the sensor to the processing device, the connector being a portion of the interconnecting circuit.

14. The magnetic tracking device of claim 9, wherein the processing device is configured to cycle the sensor between the first operating mode and the second operating mode in synchronization with a cycle of the magnetic field that is generated by the magnetic field transmitter.

15. A method comprising:
   receiving, at a processing device from a sensor configured to generate a sensor electromotive force (EMF) that measures a magnetic field that is generated by a magnetic field transmitter, a first measurement for a first operating mode in which the sensor generates the sensor EMF when receiving the magnetic field, the first measurement representing the sensor EMF and a parasitic EMF of an interconnecting circuit, wherein a switching device in parallel with the sensor is in a high impedance state in the first operating mode;
   receiving, at the processing device from the sensor, a second measurement for a second operating mode in which the sensor generates a reduced sensor EMF when receiving the magnetic field, the second measurement representing the parasitic EMF and the reduced sensor EMF, wherein the switching device is in a low impedance state in the second operating mode, wherein the second operating mode comprises a direct current (DC) component having a value that exceeds a threshold value to saturate a core of the sensor;
   comparing, by the processing device, the first measurement and the second measurement, wherein comparing the first measurement and the second measurement comprises determining a change an impedance of the interconnecting circuit in the second operating mode relative to the impedance of the interconnecting circuit in the first operating mode; and
   based on comparing the first measurement and the second measurement, determine an approximate value of the sensor EMF.

16. The method of claim 15, wherein the interconnecting circuit is configured generate the parasitic EMF in each of the first operating mode and the second operating mode when receiving the magnetic field.

17. The method of claim 16, wherein the parasitic EMF comprises induced EMF values from an interconnect loop of the interconnecting circuit, a connector loop of the interconnecting circuit, a trace loop of the interconnecting circuit, or any combination thereof.

18. The method of claim 15, further comprising determining, by the processing device, an approximate position of the sensor relative to the magnetic field transmitter based on the approximate value of the sensor EMF.

19. The method of claim 15, further comprising cycling between the first operating mode and the second operating mode in synchronization with a cycle of the magnetic field that is generated by the magnetic field transmitter.

\* \* \* \* \*